(12) United States Patent
Sakamoto et al.

(10) Patent No.: US 11,896,579 B2
(45) Date of Patent: Feb. 13, 2024

(54) COMBINATION DRUG

(71) Applicant: Chugai Seiyaku Kabushiki Kaisha, Tokyo (JP)

(72) Inventors: Hiroshi Sakamoto, Kamakura (JP); Toshiyuki Tsukaguchi, Kamakura (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 137 days.

(21) Appl. No.: 17/358,933

(22) Filed: Jun. 25, 2021

(65) Prior Publication Data
US 2021/0322380 A1    Oct. 21, 2021

Related U.S. Application Data

(62) Division of application No. 15/543,033, filed as application No. PCT/JP2016/051067 on Jan. 15, 2016, now Pat. No. 11,077,093.

(30) Foreign Application Priority Data

Jan. 16, 2015   (JP) .................. 2015-007244

(51) Int. Cl.
| | | |
|---|---|---|
| *A61K 31/404* | (2006.01) | |
| *A61K 45/06* | (2006.01) | |
| *A61K 31/4545* | (2006.01) | |
| *A61K 31/506* | (2006.01) | |
| *A61K 31/5355* | (2006.01) | |
| *A61K 39/395* | (2006.01) | |
| *A61K 31/44* | (2006.01) | |

(52) U.S. Cl.
CPC ............ *A61K 31/404* (2013.01); *A61K 31/44* (2013.01); *A61K 31/4545* (2013.01); *A61K 31/506* (2013.01); *A61K 31/5355* (2013.01); *A61K 39/395* (2013.01); *A61K 45/06* (2013.01)

(58) Field of Classification Search
CPC .............. A61K 31/404; A61K 31/4439; A61K 39/395; A61K 45/06; A61P 35/00
See application file for complete search history.

(56) References Cited

U.S. PATENT DOCUMENTS

| | | |
|---|---|---|
| 5,721,267 A | 2/1998 | Broka |
| 5,936,084 A | 8/1999 | Jirousek et al. |
| 9,126,931 B2 | 9/2015 | Kinoshita et al. |
| 9,365,514 B2 | 6/2016 | Furumoto et al. |
| 9,440,922 B2 | 9/2016 | Kinoshita et al. |
| 9,714,229 B2 | 7/2017 | Tanaka et al. |
| 10,344,014 B2 | 7/2019 | Shiraki et al. |
| 10,350,214 B2 | 7/2019 | Tomimatsu et al. |
| 2004/0072890 A1 | 4/2004 | Munro et al. |
| 2005/0107364 A1 | 5/2005 | Hutchinson et al. |
| 2006/0063790 A1 | 3/2006 | Gillman et al. |
| 2007/0031907 A1 | 2/2007 | Pinna et al. |
| 2007/0099893 A1 | 5/2007 | Boyd et al. |
| 2007/0249653 A1 | 10/2007 | Jagtap et al. |
| 2008/0058320 A1 | 3/2008 | Herold et al. |
| 2008/0095838 A1 | 4/2008 | Abou Chacra-Vernet |
| 2008/0262021 A1 | 10/2008 | Capraro et al. |
| 2009/0221555 A1 | 9/2009 | Ahmed et al. |
| 2010/0099658 A1 | 4/2010 | Kondoh et al. |
| 2012/0083488 A1 | 4/2012 | Kinoshita et al. |
| 2013/0143877 A1 | 6/2013 | Furumoto et al. |
| 2015/0150845 A1 | 6/2015 | Kinoshita et al. |
| 2015/0272958 A1 | 10/2015 | Kodama et al. |
| 2015/0307944 A1 | 10/2015 | Hout et al. |
| 2016/0317494 A1 | 11/2016 | Furumoto et al. |
| 2016/0340308 A1 | 11/2016 | Kinoshita et al. |
| 2017/0035773 A1 | 2/2017 | Tomimatsu et al. |
| 2017/0081306 A1 | 3/2017 | Tanaka et al. |
| 2017/0119781 A1 | 5/2017 | Meier et al. |
| 2017/0217927 A1 | 8/2017 | Shiraki et al. |
| 2019/0284163 A1 | 9/2019 | Shiraki et al. |
| 2020/0017442 A1 | 1/2020 | Kinoshita et al. |
| 2020/0038407 A1 | 2/2020 | Tomimatsu et al. |

FOREIGN PATENT DOCUMENTS

| | | |
|---|---|---|
| CN | 1902200 A | 1/2007 |
| EA | 001450 B1 | 4/2001 |
| EP | 2 253 318 | 11/2010 |
| JP | 08-092090 A | 4/1996 |
| JP | 2012-072140 A | 4/2012 |
| RU | 2162089 C2 | 1/2001 |
| RU | 2007141654 A | 5/2009 |
| WO | WO-00/69856 A1 | 11/2000 |
| WO | WO-2004/080980 A1 | 9/2004 |
| WO | WO-2005/009389 A2 | 2/2005 |
| WO | WO-2005/097765 A1 | 10/2005 |

(Continued)

OTHER PUBLICATIONS

Rossi et al (International Journal of Cancer vol. 45 pp. 499-508 published online 2014) (Year: 2014).*
U.S. Appl. No. 16/862,125, filed Apr. 29, 2020, Kinoshita et al.
U.S. Appl. No. 17/019,896, filed Sep. 14, 2020, Shiraki et al.
U.S. Appl. No. 17/255,707, filed Dec. 23, 2020, Kitayama et al.
U.S. Appl. No. 17/271,437, filed Sep. 3, 2019, Serizawa et al.
Arjaans et al., "Bevacizumab-Induced Normalization of Blood Vessels in Tumors Hampers Antibody Uptake," Cancer Research, Jun. 1, 2013, 73(11):3347-3355.
Asche et al., "Synthesis, antitumour activity and structure-activity relationships of 5H-benzo[b]carbazoles," Bioorganic & Medicinal Chemistry, 2005, 13:819-837.

(Continued)

*Primary Examiner* — Theodore R. Howell
*Assistant Examiner* — George W Kosturko
(74) *Attorney, Agent, or Firm* — Foley & Lardner LLP

(57) ABSTRACT

The present invention relates to a drug that is for treating or preventing cancer, that is effective in the treatment of cancer, and that comprises a combination of an ALK inhibitor and a VEGF inhibitor. The present invention also relates to a method for treating or preventing cancer and a method for inhibiting tumor growth.

20 Claims, 1 Drawing Sheet
Specification includes a Sequence Listing.

(56) References Cited

FOREIGN PATENT DOCUMENTS

| WO | WO-2006/021884 A2 | 3/2006 | | |
|---|---|---|---|---|
| WO | WO-2006/120557 A1 | 11/2006 | | |
| WO | WO-2007/023310 A2 | 3/2007 | | |
| WO | WO-2007/056497 A1 | 5/2007 | | |
| WO | WO-2007/130468 A2 | 11/2007 | | |
| WO | WO-2008/021369 A2 | 2/2008 | | |
| WO | WO-2008/051547 A1 | 5/2008 | | |
| WO | WO-2008/130951 A1 | 10/2008 | | |
| WO | WO-2009/008371 A1 | 1/2009 | | |
| WO | WO-2009/013126 A1 | 1/2009 | | |
| WO | WO-2009/073620 A2 | 6/2009 | | |
| WO | WO-2010/128324 A1 | 11/2010 | | |
| WO | WO-2010/142423 A2 | 12/2010 | | |
| WO | WO-2010/142685 A1 | 12/2010 | | |
| WO | WO-2012/042421 A1 | 4/2012 | | |
| WO | WO-2012042421 A1 * | 4/2012 | ........... | A61K 31/395 |
| WO | WO-2013132376 A1 * | 9/2013 | ............ | A61P 35/00 |

OTHER PUBLICATIONS

Awad et al., "ALK Inhibitors in Non-Small Lung Cell Cancer: Crizotinib and Beyond," Clin. Adv. Hematol. Oncol., Jul. 2014, 12(7):429-439.
Bernardo et al., "Synthesis, Electrochemistry, and Bioactivity of the Cyanobacterial Calothrixins and Related Quinones," J. Med. Chem., 2004, 47:4958-4963.
Bilsland et al., "Behavioral and Neurochemical Alterations in Mice Deficient in Anaplastic Lymphoma Kinase Suggest Therapeutic Potential for Psychiatric Indications," Neuropsychopharmacology, 2008, 33:685-700.
Boogaard et al., "Ring D Modifications of Ellipticine. Part 2. Chlorination of Ellipticine via its N-oxide and Synthesis and Selective Oxidation of 5,6,11-Trimethyl-5H-Benzo[b]Carbazole," Tetrahedron, 1994, 50(16):4811-4828.
Bunz, F., "Chapter 1, The Genetic Basis of Cancer," Principles of Cancer Genetics, 2008, 1-47.
CAS RN 100863-39-6, STN Entry Date Mar. 15, 1986.
CAS RN 222318-66-3, STN Entry Date May 7, 1999.
CAS RN 24716-14-1, STN Entry Date Nov. 16, 1984.
CAS RN 36263-63-5, STN Entry Date Nov. 16, 1984.
CAS RN 4355-38-8, STN Entry Date Nov. 16, 1984.
CAS RN 6008-29-3, STN Entry Date Nov. 16, 1984.
CAS RN 61492-49-7, STN Entry Date Nov. 16, 1984.
CAS RN 74205-47-3, STN Entry Date Nov. 16, 1984.
CAS RN 89579-57-7, STN Entry Date Nov. 16, 1984.
CAS RN 93257-39-7, STN Entry Date Dec. 18, 1984.
Chang et al., "Polymethacrylates," Handbook of Pharmaceutical Excipients, Rowe et al., Eds., 2009, 6th Ed., 525-533.
Chen et al., "Oncogenic mutations of ALK kinase in neuroblastoma," Nature, Oct. 16, 2008, 455:971-974, and Methods page.
Ciamporcero et al., "Combination Strategy Targeting VEGF and HGF/c-met in Human Renal Cell Carcinoma Models," Molecular Cancer Therapeutics, Nov. 7, 2014, 14(1):101-110.
Cools et al., "Identification of Novel Fusion Partners of ALK, the Anaplastic Lymphoma Kinase, in Anaplastic Large-Cell Lymphoma and Inflammatory Myofibroblastic Tumor," Genes, Chromosomes & Cancer, 2002, 34:354-362.
Database Accession No. 1:1259(XP55784247), RN 826-55-1, 1907, one page.
Database Accession No. 27:43772 (XP55784257), RN 37828-19-6 CA, 1933, one page.
Database Accession No. 28:22560 (XP55784253), RN 77-55-4, 1934, one page.
Database Accession No. 28:22560 (XP55784254), RN 1135-67-7, 1934, one page.
Database Accession No. 41:3570(XP55784249), RN 6120-95-2, 1946, one page.
Davies, Peter, "Oral Solid Dosage Forms," Drugs and the Pharmaceutical Sciences, Pharmaceutical Preformulation and Formulation, Mark Gibson, Ed., 2009, 2nd Edition, 199:367-430.
Defendant Fresenius Kabi USA, LLC's Initial Invalidity Contentions, filed Oct. 9, 2020 in C.A. No. 20-394 (RGA), *Hoffmann-LaRoche, Inc., Chugai Pharmaceutical Co., Ltd., and Genentech, Inc.* (Plaintiffs and Counterclaim Defendants) v. *Fresenius Kabi USA, LLC* (Defendant and Counterclaim Plantiff), 112 pages.
Druker et al., "Section 1: Chronic Myelogenous Leukemia," Cancer: Principles & Practice of Oncology, 7th Edition (DeVita et al., Eds.), 2121.
Faderl et al., "Section 3: Myelodysplastic Syndromes," Cancer: Principles & Practice of Oncology, 7th Edition (DeVita et al., Eds.), 2144.
Fine et al., "Section 2: Neoplasms of the Central Nervous System," Cancer: Principles & Practice of Oncology, 7th Edition (DeVita et al., Eds.), 1834-1887.
Fischer et al., "A Ki-1(CD30)-Positive Human Cell Line (Karpas 299) Established From a High-Grade Non-Hodgkin's Lymphoma, Showing a 2;5 Translocation and Rearrangement of the T-Cell Receptor β-Chain Gene," Blood, Jul. 1988, 72(1):234-240.
Gadgeel et al., "A Phase 1 Dose Escalation Study of a New ALK Inhibitor, CH5424802/RO5424802, in ALK Non-Small Cell Lung Cancer (NSCLC) Patients who have Failed Crizotinib (AF-002JG/NP28761, NCT01588028)," Journal of Thoracic Oncology, Nov. 2013, 8(2):S199, Abstract O16.06.
Gadgeel et al., "Safety and activity of alectinib against systemic disease and brain metastases in patients with crizotinib-resistant ALK-rearranged non-small-cell lung cancer (AF-002JG): results from the dose-finding portion of a phase 1/2 study," Lancet Oncology, 2014, 15:1119-1128.
Galkin et al., "Identification of NVP-TAE684, a potent, selective and efficacious inhibitor of NPM-ALK," PNAS, Jan. 2, 2007, 104(1):270-275.
Galkin et al., "Identification of NVP-TAE684, a potent, selective and efficacious inhibitor of NPM-ALK," PNAS, Jan. 2, 2007, 104(1):270-275 (and Corrections published in PNAS, Feb. 6, 2007, 104(6):2024-2025).
Garbett et al., "Extending Nature's Leads: The Anticancer Agent Ellipticine," Curr. Med. Chem.—Anti-Cancer Agents, 2004, 4:149-172.
George et al., "Activating mutations in ALK provide a therapeutic target in neuroblastoma," Nature, 2008, 455:975-978.
Girouard et al., "Neurovascular coupling in the normal brain and in hypertension, stroke, and Alzheimer disease," Journal of Applied Physiology, 2006, 100:328-335.
Glick et al., "Treatment with atypical antipsychotics: new indications and new populations," Journal of Psychiatric Research, 2001, 35:187-191.
Goel et al., "Mice transgenic for BRAF V600E demonstrate phenotype affecting melanocyte and neural lineages," Proceedings of the American Association for Cancer Research, Apr. 2006, 47:#273.
Goodman & Gilman's, Chemotherapy of Neoplastic Diseases, The Pharmacological Basis of Therapeutics, Brunton et al., Eds., 2008, 11th Ed., 853-908.
Griffin et al., "Recurrent Involvement of 2p23 in Inflammatory Myofibroblastic Tumors," Cancer Research, Jun. 15, 1999, 59:2776-2780.
Gunby et al., "Structural Insights into the ATP Binding Pocket of the Anaplastic Lymphoma Kinase by Site-Directed Mutagenesis, Inhibitor Binding Analysis, and Homology Modeling," J. Med. Chem., 2006, 49:5759-5768.
Hecht et al., "A Randomized Phase IIIB Trial of Chemotherapy, Bevacizumab, and Panitumumab Compared with Chemotherapy and Bevacizumab Alone for Metastatic Colorectal Cancer," Journal of Clinical Oncology, Feb. 10, 2009, 27(5):672-680.
Herbst et al., "ALK Gene Products in Anaplastic Large Cell Lymphomas and Hodgkin's Disease," Blood, Sep. 1, 1995, 86(5):1694-1700.
Hibino et al., "Intrinsic and acquired resistance mechanisms of alectinib in ALK rearranged cells," AACR Annual Meeting, Apr. 5-9, 2014, Abstract 3720 (Cancer Res., Oct. 1, 2014, 74:3720).

(56) References Cited

OTHER PUBLICATIONS

Hida et al., "Pharmacologic study (JP28927) of alectinib in Japanese patients with ALK non-small-cell lung cancer with or without prior crizotinib therapy," Cancer Science, 2016, 107:1642-1646.

Hooton, J.C., "Carboxymethylcellulose Calcium," Handbook of Pharmaceutical Excipients, Rowe et al., Eds., 6th Ed., 2009, 117-118.

Huang et al., "An in vivo model to study human GSTP1 polymorphisms in osteosarcoma," Proceedings of the American Association for Cancer Research, Apr. 2006, 47:#271.

Hübinger et al., "CD30-mediated cell cycle arrest associated with induced expression of p21CIP1/WAF1 in the anaplastic large cell lymphoma cell line Karpas 299," Oncogene, 2001, 20:590-598.

Inoue et al., "One-year Follow-up of a Phase I/II Study of a Highly Selective ALK Inhibitor CH5424802/RO5424802 in ALK-Rearranged Advanced Non-Small Cell Lung Cancer (NSCLC)," Journal of Thoracic Oncology, Nov. 2013, 8(Supp.2):S1204, Abstract P3.11-034.

Jazii et al., "Identification of squamous cell carcinoma associated proteins by proteomics and loss of beta tropomyosin expression in esophageal cancer," World J. Gastroenterol., Nov. 28, 2006, 12(44):7104-7112.

Kabir et al., "Hydroxypropyl Cellulose," Handbook of Pharmaceutical Excipients, Rowe et al., Eds., 6th Ed., 2009, 317-322.

Kanayama, Hiroomi, "VEGFR Targeted Therapy for Advanced Renal Cell Carcinoma, Present and Future Strategy," Experimental Medicine, 2011, 29(2):359-366, with English translation.

Kashyap et al., "Fast Disintegrating Tablet: A Boon to Pediatric and Geriatric," International Journal of Pharma Professional's Research, Apr. 2011, 2(2):318-326.

Kimura et al., "ALK fusion gene positive lung cancer and 3 cases treated with an inhibitor for ALK kinase activity," Lung Cancer, Jan. 2012, 75(1):66-72.

Kinoshita et al., "Design and synthesis of a highly selective, orally active and potent anaplastic lymphoma kinase inhibitor (CH5424802)," Bioorganic & Medicinal Chemistry, 2012, 20:1271-1280.

Kirsch, Gilbert H., "Heterocyclic Analogues of Carbazole Alkaloids," Current Organic Chemistry, 2001, 5:507-518.

Knoelker et al., "Transition Metal Complexes in Organic Synthesis, Part 38. First Total Synthesis of Carbazomycin G and H," Tetrahedron Letters, 1997, 38(23):4051-4054.

Kodama et al., "Antitumor activity of the selective ALK inhibitor alectinib in models of intracranial metastases," Cancer Chemotherapy Pharmacol., 2014, 74:1023-1028.

Kuppen et al., "Tumor structure and extracellular matrix as a possible barrier for therapeutic approaches using immune cells or adenoviruses in colorectal cancer," Histochem. Cell. Biol., 2001, 115:67-72.

Kuster, Bernhard, Ed., Kinase Inhibitors, Methods and Protocols, Methods in Molecular Biology, 2012, vol. 795, Chapter 1 by Fabbro et al., "Targeting Cancer with Small-Molecular-Weight Kinase Inhibitors."

Kwak et al., "Anaplastic Lymphoma Kinase Inhibition in Non-Small-Cell Lung Cancer," The New England Journal of Medicine, Oct. 28, 2010, 363(18):1693-1703.

Lamant et al., "Establishment of a novel anaplastic large-cell lymphoma-cell line (COST) from a 'small-cell variant' of ALCL," Leukemia, 2004, 18:1693-1698.

Li et al., "Design and Synthesis of 5-Aryl-pyridone-carboxamides as Inhibitors of Anaplastic Lymphoma Kinase," J. Med. Chem., 2006, 49:1006-1015.

Li et al., "Development of Anaplastic Lymphoma Kinase (ALK) Small-Molecule Inhibitors for Cancer Therapy," Medicinal Research Reviews, 2008 (online Aug. 10, 2007), 23(3):372-412.

Liao, Jeffrey Jie-Lou, "Molecular Recognition of Protein Kinase Binding Pockets for Design of Potent and Selective Kinase Inhibitors," Journal of Medicinal Chemistry, Feb. 8, 2007, 50(3):409-424.

Lissoni et al., "Biotherapy with the pineal hormone melatonin plus aloe and myrrh tincture in untreatable metastatic cancer patients as an essence therapy of cancer," Cancer Therapy, 2009, 7:397-401.

Luo et al., "Principles of Cancer Therapy: Oncogene and Non-oncogene Addiction," Cell, Mar. 6, 2009, 136:823-837.

Ma et al., "Current Status of Targeted Therapy for Anaplastic Lymphoma Kinase in Non-small Cell Lung Cancer," Chin. J. Lung Cancer, Dec. 2014, 17(12):850-854, with English abstract.

Martinengo et al., "ALK-Dependent Control of Hypoxia-Inducible Factors Mediates Tumor Growth and Metastasis," Molecular and Cellular Pathobiology, Cancer Research, Sep. 5, 2014, 74(21):6094-6106.

Mosse et al., "Identification of ALK as a major familial neuroblastoma predisposition gene," Nature, Oct. 16, 2008, 455:930-935, and Methods page.

Nakade et al., "Triple Inhibition of EGFR, Met, and VEGF Suppresses Regrowth of HGF-Triggered, Erlotinib-Resistant Lung Cancer Harboring an EGFR Mutation," Journal of Thoracic Oncology, Jun. 2014, 9(6):775-783.

Nakagawa et al., "A phase I/II study with a highly selective ALK inhibitor CH5424802/RO5424802 in ALK-positive non-small cell lung cancer (NSCLC) patients: Updated safety and efficacy results from AF-001JP," 49th Annual Meeting of the American Society of Clinical Oncology (ASCO), Chicago, IL, May 31, 2013-Jun. 4, 2013, poster, Abstract No. 8033.

Nakagawa et al., "Antitumor Activity of alectinib (CH5424802/RO5424802) for ALK-Rearranged NSCLC with or without Prior crizotinib Treatment in Bioequivalence Study," 49th Annual Meeting of the American Society of Clinical Oncology (ASCO), Chicago, IL, May 31, 2013-Jun. 4, 2013, poster, Abstract No. 8033.

National Cancer Institute, http://www.cancer.gov/, "A to Z List of Cancers," downloaded May 29, 2014, 22 pages.

O'Brien et al., "Section 2: Chronic Lymphoid Leukemias," Cancer: Principles & Practice of Oncology, 7th Edition (DeVita et al., Eds.), 2005, 2133.

O'Brien et al., "Vascular cognitive impairment," The Lancet Neurology, Feb. 2003, 2:89-98.

Ou et al., "Consistent Therapeutic Efficacy of CH5424802/RO5424802 in Brain Metastases Among Crizotinib-Refractory ALK-Positive Non-small Cell Lung Cancer (NSCLC) Patients in an Ongoing Phase I/II Study (AF-002JG/NP28761, NCT01588028)," Journal of Thoracic Oncology, Nov. 2013, 8(2):Abstract O17.07.

Pao et al., "EGF receptor gene mutations are common in lung cancers from 'never smokers' and are associated with sensitivity of tumors to gefitinib and erlotinib," PNAS, Sep. 7, 2004, 101(36):13306-13311.

Piva et al., "Ablation of oncogenic ALK is a viable therapeutic approach for anaplastic large-cell lymphomas," Blood, Jan. 2006, 107(2):689-697.

Plumb, P., "Sodium Lauryl Sulfate," Handbook of Pharmaceutical Excipients, Rowe et al., Eds., 6th Ed., 2009, 652-653.

Rao et al., "Choroidal Metastases from ELM4-ALK-Positive Non-Small Lung Adenocarcinoma," Journal of Clinical Oncology, Apr. 14, 2015, 33(30):e112-e114.

Rosenwald et al., "t(1;2)(q21;p23) and t(2;3)(p23;q21): Two Novel Variant Translocations of the t(2;5)(p23;q35) in Anaplastic Large Cell Lymphoma," Blood, Jul. 1, 1999, 94(1):362-364.

Rossi et al., "ALK inhibitors and advanced non-small cell lung cancer (Review)," International Journal of Oncology, 2014, 45:499-508.

Sakamoto, Hiroshi, "ALK Inhibitors," Folia Pharmacologica Japonica, 2013, 142(1):48-50, with English translation.

Scheinberg et al., "Section 2: Management of Acute Leukemias," Cancer: Principles & Practice of Oncology, 7th Edition (DeVita et al., Eds.), 2005, 2088, 2092.

Sennino et al., "Suppression of Tumor Invasion and Metastasis by Concurrent Inhibition of c-Met and VEGF Signaling in Pancreatic Neuroendocrine Tumors," Cancer Discov., Mar. 2012, 2(3):270-287.

Seto et al., "CH5424802 (RO5424802) for patients with ALK-rearranged advanced non-small-cell lung cancer (AF-001JP study): a single-arm, open-label, phase 1-2 study," Lancet Oncology, Jun. 2013, 14:590-598.

Seto et al., "Erlotinib alone or with bevacizumab as first-line therapy in patients with advanced non-squamous non-small-cell lung cancer

(56) References Cited

OTHER PUBLICATIONS harbouring EGFR mutations (J025567): an open-label, randomized, multicenter, phase 2 study," The Lancet, Oct. 2014, 15:1236-1244.
Shah et al., "Current approaches in the treatment of Alzheimer's disease," Biomedicine & Pharmacotherapy, 2008, 62:199-207.
Shaw et al., "Targeting Anaplastic Lymphoma Kinase in Lung Cancer," Clinical Cancer Research, 2011, 17:2081-2086.
Sheridan, Robert P., "The Most Common Chemical Replacements in Drug-Like Compounds," J. Chem. Inf. Comput. Sci., 2002, 42:103-108.
Shujuan, Wang, "The new insights on the diagnosis of malignant histiocytosis," Chinese Journal of Laboratory Medicine, Jan. 30, 2005, 28(1):14-16.
Silverman, Richard B., The Organic Chemistry of Drug Design and Drug Action, Second Ed., Elsevier Academic Press, Northwestern University, Evanston, Illinois, 2004, 29-31, table 2.2.
Soda et al., "Identification of the transforming EML4-ALK fusion gene in non-small-cell lung cancer," Nature, Aug. 2, 2007, 448:561-566, and Methods page.
Soussi, Thierry, "p53 Antibodies in the Sera of Patients with Various Types of Cancer: A Review," Cancer Res., 2000, 60:1777-1788.
Stoica et al., "Identification of Anaplastic Lymphoma Kinase as a Receptor for the Growth Factor Pleiotrophin," J. Biol. Chem., May 18, 2001, 276(20:16772-16779.
Stoica et al., "Midkine Binds to Anaplastic Lymphoma Kinase (ALK) and Acts as a Growth Factor for Different Cell Types," J. Biol. Chem., Sep. 27, 2002, 277(39):35990-35998.
Subbiah et al., "Activity of c-Met/ALK Inhibitor Crizotinib and Multi-Kinase VEGF Inhibitor Pazopanib in Metastatic Gastrointestinal Neuroectodermal Tumor Harboring EWSR1-CREB1 Fusion," Oncology, 2016, 91(6):348-353.
Subbiah et al., "STUMP un"stumped": anti-tumor response to anaplastic lymphoma kinase (ALK) inhibitor based targeted therapy in uterine inflammatory myofibroblastic tumor with myxoid features harboring DCTN1-ALK fusion," Journal of Hematology and Oncology, Jun. 11, 2015, 8:66, 1-7.
Sugawara et al., "Identification of Anaplastic Lymphoma Kinase Fusions in Renal Cancer," Cancer, Sep. 15, 2012, 118:4427-4436.
Toyokawa et al., "ALK Inhibitors: What Is the Best Way to Treat Patients With ALK+ Non-Small-Cell Lung Cancer," Clinical Lung Cancer, Jun. 2, 2014, 15(5):313-319.
Van Der Veldt et al., "Rapid Decrease in Delivery of Chemotherapy to Tumors after Anti-VEGF Therapy: Implications for Scheduling of Anti-Angiogenic Drugs," Cancer Cell, Jan. 17, 2012, 21:82-91.
Vendome et al., "Molecular Modeling of Wild-Type and D816V c-Kit Inhibition Based on ATP-Competitive Binding of Ellipticine Derivatives to Tyrosine Kinases," J. Med. Chem., 2005, 48:6194-6201.
Wanner et al., "A convenient synthesis of 6-methylellipticine and 6-methylolivacine," Heterocycles, 1982, 19(12):2295-2300.
Wendling, Patrice, "Alectinib active in ALK-positive, crizotinib-refractory NSCLC," Chest Physician, Oct. 9, 2013, 4 pages.
Wood et al., "Lack of the t(2;5) or Other Mutations Resulting in Expression of Anaplastic Lymphoma Kinase Catalytic Domain in CD30+ Primary Cutaneous Lymphoproliferative Disorders and Hodgkin's Disease," Blood, Sep. 1, 1996, 88(5):1765-1770.
Yanagitani et al., "ALK Inhibitors," Pharma Medica, 2014, 32(11):33-35, with English translation.
Zhao et al., "The progress of the research on anaplastic lymphoma kinase genetic abnormality of anaplastic large cell lymphoma," Foreign Medical Sciences (Section of Blood Transfusion and Heanatology), Oct. 15, 2004, 27(5):403-406.

\* cited by examiner

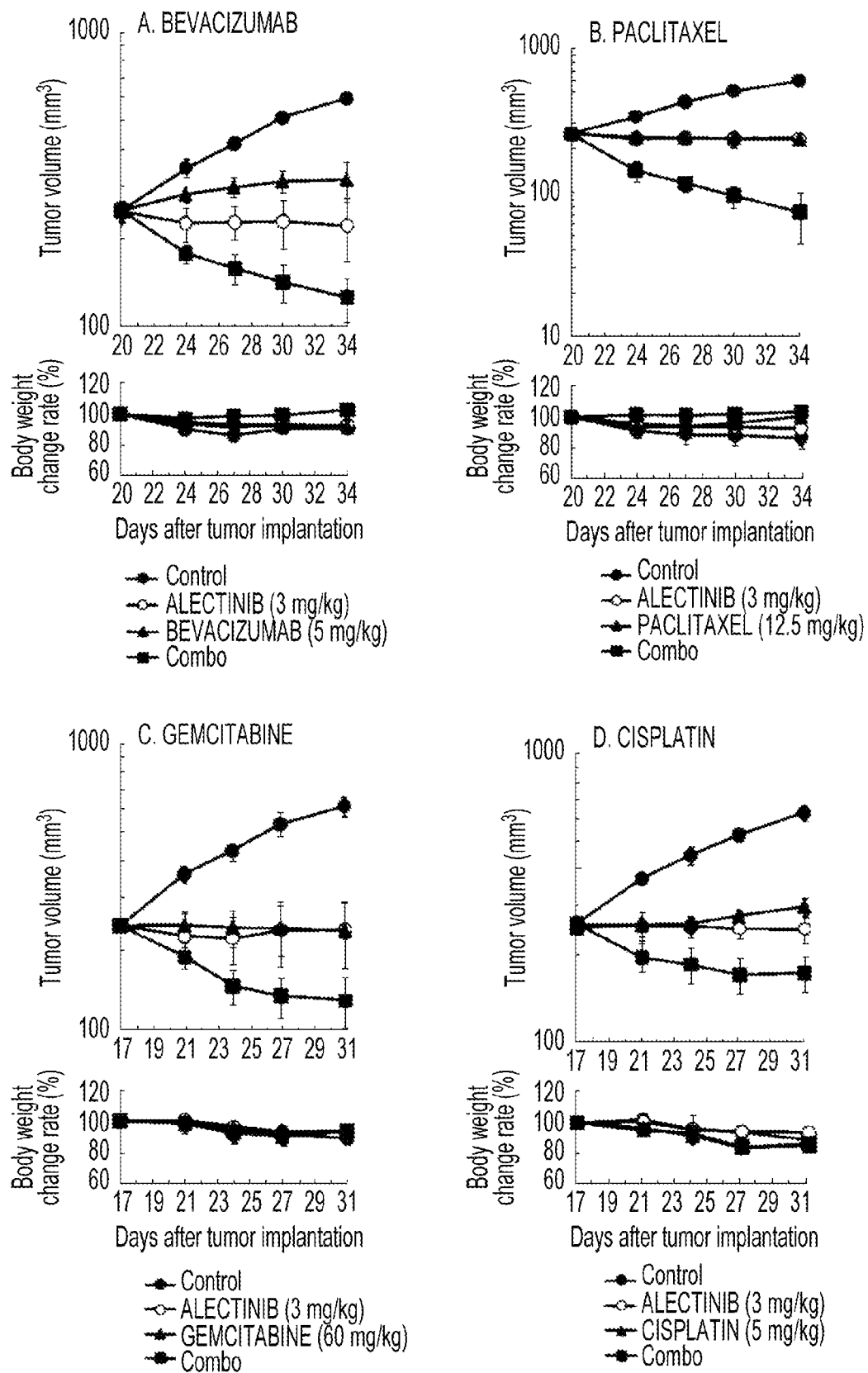

COMBINATION DRUG

CROSS-REFERENCE TO RELATED APPLICATIONS

This application is a Divisional of U.S. application Ser. No. 15/543,033, which is the U.S. National Stage of PCT/JP2016/051067, filed Jan. 15, 2016, which claims priority to JP 2015-007244, filed Jan. 16, 2015.

The instant application contains a Sequence Listing which has been submitted in ASCII format via EFS-WEB and is hereby incorporated by reference in its entirety. Said ASCII copy, created on Jun. 23, 2021, is named sequence.txt and is 2,419 bytes.

TECHNICAL FIELD

The present invention relates to medicaments produced by combining an ALK inhibitor and a VEGF inhibitor, methods of treating or preventing cancers, and products, which are useful for treating or preventing cancers.

BACKGROUND ART

Anaplastic Lymphoma Kinase (ALK) is a receptor tyrosine kinase belonging to the insulin receptor family (NPL 1, NPL 2).

Abnormalities (translocations, point mutations and gene multiplication) of the ALK gene have been reported to result in the generation of an abnormal kinase fused with another gene, which is involved in carcinogenesis.

ALK inhibitors that have been approved in Japan or any other country include Alecensa™ (generic name: alectinib hydrochloride, Alectinib), Xalkori™ (generic name: crizotinib), and Zykadia™ (generic name: ceritinib).

In using anti-cancer agents, a plurality of anti-cancer agents with different modes of action have been widely used in order to enhance their effects, expand the spectrum of applicable tumors, or cope with or prevent cancers that have acquired resistance.

There have been reports of a combined use of alectinib, an ALK inhibitor, and other molecular targeted agent. It has been reported that as a result of a combined use of alectinib and erlotinib (a selective tyrosine kinase inhibitor against EGFR (epidermal growth factor receptor)) or crizotinib (a tyrosine kinase inhibitor against ALK and c-Met (hepatocyte growth factor receptor)) tumor regression was observed in models xenotransplanted with alectinib-resistant lung cancer cell line (NPL 3: Cancer Res Oct. 1, 2014, 74; 3720, AACR Annual Meeting 2014; Apr. 5-9, 2014, Abstract 3720).

On the other hand, vascular endothelial growth factor (VEGF) is a major regulatory factor of angiogenesis. In most human tumors, the VEGF expression is enhanced and VEGF is involved in tumor growth and metastasis. It has been verified that blocking of the VEGF signaling pathway is effective in suppression of angiogenesis in tumor tissues by VEGF, inhibition of tumor growth, normalization of vasculature, reduction of vascular permeability, and reduction of the increased interstitial pressure in tumor tissues. Examples of VEGF pathway inhibitors include AVASTIN™ (generic name: bevacizumab), NEXAVAR™ (generic name: sorafenib), VOTRIENT™ (generic name: pazopanib hydrochloride), SUTENT™ (generic name: sunitinib malate), INLYTA™ (generic name: axitinib), and STIVARGA™ (regorafenib hydrate). Among VEGF pathway inhibitors which have been developed as anti-cancer agents, ramucirumab, cabozantinib maleate (cabozantinib S-malate), and nintedanib ethanesulfonate (nintedanib esylate), all of which are generic names, are sold as anti-cancer agents.

AVASTIN (bevacizumab) has been approved in Japan to be given in combination with certain standard chemotherapies or chemotherapeutic agents for unresectable advanced/recurrent colorectal cancer, unresectable advanced/recurrent non-small cell lung cancer except for squamous cell cancer, ovarian cancer, and inoperable or recurrent breast cancer. AVASTIN (bevacizumab), however, has not yet been approved to be given in combination with any molecular targeted agent other than VEGF pathway inhibitors at the present, but an effect of a combined use of a VEGF pathway inhibitor and erlotinib which is a selective tyrosine kinase inhibitor against EGFR as well as an effect of tumor suppression by inhibiting both VEGF pathway and c-Met or HGF/c-Met pathway have been reported (NPL 4: Lancet Oncol 2014; 15:1236-44, NPL 5: Cancer Discov. 2012 March; 2(3):270-287, and NPL 6: Mol Cancer Ther. 2015 January; 14(1):101-110, "Combination strategy targeting VEGF and HGF/c-met in human renal cell carcinoma models").

No article, however, has reported a combination of a VEGF pathway inhibitor and an ALK inhibitor until now. Furthermore, it has been reported that administration of bevacizumab could possibly degrade the property of a medicine used in combination to penetrate into tumors (NPL 7: Cancer Cell 21, 82-91, Jan. 17, 2012, and NPL 8: Cancer Res. 2013 Jun. 1; 73(11):3347-55 "Bevacizumab-induced normalization of blood vessels in tumors hampers antibody uptake"), and inhibition of angiogenesis can reduce an effect of a medicine used in combination. In clinical practices, it has been reported that the progression-free survival was reduced in a clinical trial using panitumumab, which is an anti-EGFR1 antibody, bevacizumab and chemotherapy (NPL 9: Journal of Clinical Oncology, volume 27, no. 5, Feb. 10, 2009, 672-680).

CITATION LIST

Non-Patent Literature

NPL 1: Proc Natl Acad Sci USA, 101, 13306-13311, 2004
NPL 2: Nature, 448, 561-566, 2007
NPL 3: Cancer Res Oct. 1, 2014, 74; 3720, AACR Annual Meeting 2014; Apr. 5-9, 2014, Abstract 3720
NPL 4: Lancet Oncol 2014; 15:1236-44
NPL 5: Cancer Discov. 2012 March; 2(3):270-287
NPL 6: Mol Cancer Ther. 2015 January; 14(1):101-110
NPL 7: Cancer Cell 21, 82-91, Jan. 17, 2012
NPL 8: Cancer Res. 2013 Jun. 1; 73(11): 3347-3355
NPL 9: Journal of Clinical Oncology, volume 27, no. 5, Feb. 10, 2009, 672-680

SUMMARY OF INVENTION

Technical Problem

Development of medicaments useful for preventing and treating cancers and have excellent efficacy is thus desired.

An object of the present invention is to provide novel medicaments produced by combining a plurality of agents, methods of treating cancers and products using the same, for use in treating and/or preventing various cancers as well as extending progression-free survival.

Solution to Problem

The present inventors unexpectedly found that, as a result of using a combination of an ALK inhibitor and a VEGF inhibitor, a combined use of these pharmaceutical agents provided better tumor response than in cases where each of these agents was administered alone, and the present invention was thus completed.

Specifically, the present invention the following invention:

[1]
A medicament for treating or preventing a cancer, the medicament being produced by combining an ALK inhibitor and a VEGF inhibitor.

[2]
The medicament according to [1], wherein the medicament is formulated in a single dosage form.

[3]
The medicament according to [1], wherein the ALK inhibitor and the VEGF inhibitor are administered in separate dosage forms.

[4]
The medicament according to [3], wherein the ALK inhibitor and the VEGF inhibitor are administered simultaneously or sequentially.

[5]
A medicament for treating or preventing a cancer, the medicament being used with a VEGF inhibitor, including an ALK inhibitor as an active ingredient.

[6]
The medicament according to [5], wherein the medicament is administered simultaneously with the VEGF inhibitor.

[7]
The medicament according to [5], wherein the medicament is administered prior to or after the administration of the VEGF inhibitor.

[8]
A medicament for treating or preventing a cancer, the medicament being used with an ALK inhibitor, including a VEGF inhibitor as an active ingredient.

[9]
The medicament according to [8], wherein the medicament is administered simultaneously with the ALK inhibitor.

[10]
The medicament according to [8], wherein the medicament is administered prior to or after the administration of the ALK inhibitor.

[11]
The medicament according to any one of [1] to [10], wherein the ALK inhibitor is a compound selected from the group consisting of alectinib, crizotinib, and ceritinib, or a salt thereof.

[12]
The medicament according to any one of [1] to [11], wherein the ALK inhibitor is alectinib or a salt thereof.

[13]
The medicament according to [12], wherein the alectinib or a salt thereof is administered at a dose of 20 mg, 40 mg, 60 mg, 80 mg, 120 mg, 160 mg, 220 mg, 240 mg, 300 mg, 460 mg, 600 mg, 760 mg or 900 mg calculated as a free form twice a day.

[14]
The medicament according to any one of [1] to [13], wherein the VEGF inhibitor is selected from the group consisting of bevacizumab, sorafenib, and sunitinib.

[15]
The medicament according to any one of [1] to [13], wherein the VEGF inhibitor is an anti-VEGF antibody.

[16]
The medicament according to [15], wherein the anti-VEGF antibody includes a heavy chain variable region and a light chain variable region,
the heavy chain variable region produced so as to include the following amino acid sequence:

```
                                    (SEQ ID NO.: 1)
EVQLVESGGG LVQPGGSLRL SCAASGYTFT NYGMNWVRQA

PGKGLEWVGW INTYTGEPTY AADFKRRFTF SLDTSKSTAY

LQMNSLRAED TAVYYCAKYP HYYGSSHWYF DVWGQGTLVT

VSS;
``` the light chain variable region produced so as to include the following amino acid sequence:

```
                                    (SEQ ID NO.: 2)
DIQMTQSPSS LSASVGDRVT ITCSASQDIS NYLNWYQQKP

GKAPKVLIYF TSSLHSGVPS RFSGSGSGTD FTLTISSLQP

EDFATYYCQQ YSTVPWTFGQ GTKVEIKR.
```

[17]
The medicament according to [16], wherein the anti-VEGF antibody is administered at a dose of between 1 μg/kg and 50 mg/kg.

[18]
The medicament according to [17], wherein the anti-VEGF antibody is administered at a dose of 5 mg/kg, 7.5 mg/kg, 10 mg/kg or 15 mg/kg.

[19]
The medicament according to any one of [16] to [18], wherein the anti-VEGF antibody is administered once a week, once every two weeks, or once every three weeks.

[20]
The medicament according to any one of [1] to [19], wherein the cancer is selected from the group consisting of non-Hodgkin's lymphoma, neuroblastoma, inflammatory myofibroblastic tumor, renal cancer, and lung cancer.

[21]
The medicament according to any one of [1] to [20], wherein the cancer is positive for an ALK fusion gene.

[22]
A method of treating or preventing a cancer including: administering, in combination, an effective amount of ALK inhibitor and an effective amount of VEGF inhibitor to a subject.

[23]
The method according to [22], wherein the ALK inhibitor and the VEGF inhibitor are administered in separate dosage forms.

[24]
The method according to [23], wherein the ALK inhibitor and the VEGF inhibitor are administered simultaneously or sequentially.

[25]
A method of enhancing a therapeutic effect of an ALK inhibitor on a cancer, the method including: administering an effective amount of VEGF inhibitor to a subject.

[26]
The method according to [25], wherein the VEGF inhibitor is administered simultaneously with the ALK inhibitor.

[27]
The method according to [26], wherein the VEGF inhibitor is administered prior to or after the administration of the ALK inhibitor.

[28]

A method of extending a tumor progression-free survival including: administering, in combination, an effective amount of ALK inhibitor and an effective amount of VEGF inhibitor to a subject.

[29]

The method according to [28], wherein the ALK inhibitor and the VEGF inhibitor are administered in separate dosage forms.

[30]

The method according to [29], wherein the ALK inhibitor and the VEGF inhibitor are administered simultaneously or sequentially.

[31]

The method according to any one of [22] to [30], wherein the cancer is selected from the group consisting of non-Hodgkin's lymphoma, neuroblastoma, inflammatory myofibroblastic tumor, renal cancer, and lung cancer.

[32]

The method according to any one of [22] to [30], wherein the cancer is positive for an ALK fusion gene.

[33]

A method of suppressing growth of a tumor including: administering, in combination, an effective amount of ALK inhibitor and an effective amount of VEGF inhibitor to a subject.

[34]

The method according to [33], wherein the ALK inhibitor and the VEGF inhibitor are administered in separate dosage forms.

[35]

The method according to [34], wherein the ALK inhibitor and the VEGF inhibitor are administered simultaneously or sequentially.

[36]

The method according to any one of [33] to [35], wherein the tumor is selected from the group consisting of non-Hodgkin's lymphoma, neuroblastoma, inflammatory myofibroblastic tumor, renal cancer, and lung cancer.

[37]

The method according to any one of [33] to [35], wherein the tumor has an ALK fusion gene.

[38]

The method according to any one of [22] to [37], wherein the ALK inhibitor is a compound selected from the formulae (I) to (III), or a salt thereof:

[39]

The method according to any one of [22] to [37], wherein the ALK inhibitor is a compound selected from the group consisting of alectinib, crizotinib, and ceritinib, or a salt thereof.

[40]

The method according to [22] to [37], wherein the ALK inhibitor is alectinib or a salt thereof.

[41]

The method according to [40], wherein the alectinib or a salt thereof is administered at a dose of 20 mg, 40 mg, 60 mg, 80 mg, 120 mg, 160 mg, 220 mg, 240 mg, 300 mg, 460 mg, 600 mg, 760 mg or 900 mg calculated as a free form twice a day.

[42]

The method according to any one of [22] to [41], wherein the VEGF inhibitor is bevacizumab, sorafenib, or sunitinib.

[43]

The method according to any one of [22] to [41], wherein the VEGF inhibitor is an anti-VEGF antibody.

[44]

The method according to [43], wherein the anti-VEGF antibody is a humanized antibody.

[45]

The method according to [44], wherein the anti-VEGF antibody includes a heavy chain variable region and a light chain variable region, the heavy chain variable region produced so as to include the following amino acid sequence:

```
                                        (SEQ ID NO.: 1)
EVQLVESGGG LVQPGGSLRL SCAASGYTFT NYGMNWVRQA

PGKGLEWVGW INTYTGEPTY AADFKRRFTF SLDTSKSTAY

LQMNSLRAED TAVYYCAKYP HYYGSSHWYF DVWGQGTLVT

VSS;
``` the light chain variable region produced so as to include the following amino acid sequence:

```
                                        (SEQ ID NO.: 2)
DIQMTQSPSS LSASVGDRVT ITCSASQDIS NYLNWYQQKP

GKAPKVLIYF TSSLHSGVPS RFSGSGSGTD FTLTISSLQP

EDFATYYCQQ YSTVPWTFGQ GTKVEIKR.
```

[46]
The method according to [45], wherein the anti-VEGF antibody is bevacizumab.

[47]
The method according to any one of [42] to [46], wherein the anti-VEGF antibody is administered at 1 µg/kg to 50 mg/kg.

[48]
The method according to [47], wherein the anti-VEGF antibody is administered at 5 mg/kg, 7.5 mg/kg, 10 mg/kg or 15 mg/kg.

[49]
The method according to [47] or [48], wherein the anti-VEGF antibody is administered once a week, once every two weeks, or once every three weeks.

[50]
A product including (1) a formulated agent containing a VEGF inhibitor, (2) a container, and (3) an instruction leaflet or label indicating that the VEGF inhibitor and at least one ALK inhibitor are administered in combination to a subject to treat a cancer.

[51]
A product including (1) a formulated agent containing an ALK inhibitor, (2) a container, and (3) an instruction leaflet or label indicating that the ALK inhibitor and at least one VEGF inhibitor are administered in combination to a subject to treat a cancer.

BRIEF DESCRIPTION OF DRAWINGS

The FIGURE is a graph showing changes in tumor volume, when using a human non-small cell lung cancer cell line NCI-H2228 which is positive for the ALK fusion gene, by administration of alectinib alone and administration of (A) cisplatin, (B) paclitaxel, (C) gemcitabine, and (D) bevacizumab alone and in combination with alectinib.

DESCRIPTION OF EMBODIMENTS

The present invention relates to medicaments for treating or preventing cancers, which are produced by combining an ALK inhibitor and a VEGF inhibitor, methods of treating or preventing cancers, or methods of inhibiting tumor growth, all of which are effective for treating cancers.

ALK Inhibitors

ALK inhibitors used in the present invention refer to substances that can directly or indirectly neutralize, block, inhibit, reduce, or interfere with ALK activity. Examples of the activities of ALK include tyrosine kinase activity. The substances include low molecular weight compounds, antibodies, antisense, transcription inhibitors, and small interfering RNAs (siRNAs).

Examples of the low molecular weight compounds include those described in WO2010/143664, WO2004/076412, WO2006/021881, and WO2008/073687 and salts thereof.

Specific examples include compounds selected from the group consisting of alectinib (compound name: 9-ethyl-6,6-dimethyl-8-[4-(morpholin-4-yl)-piperidin-1-yl]-11-oxo-6,11-dihydro-5H-benzo[b]carbazole-3-carbonitrile monohydrochloride), crizotinib (compound name: 3-[(1R)-1-(2,6-dichloro-3-fluorophenyl)ethoxy]-5-[1-(piperidin-4-yl)-1H-pyrazol-4-yl]pyridin-2-amine), and serechinibu (compound name: 5-chloro-N2-(2-isopropoxy-5-methyl-4-piperidin-4-yl-phenyl)-N4-[2-(propane-2-sulfonyl)-phenyl]-pyrimidine-2,4-diamine, and salts thereof. These compounds and salts thereof can be produced using methods described in, for example, WO2010/143664, WO2004/076412, WO2006/021881, and WO2008/073687. These compounds or salts thereof also include their hydrates and pharmaceutically acceptable solvates and crystal polymorphs.

Structural formulae of alectinib, crizotinib and serechinibu are given below as formulae (I) to (III).

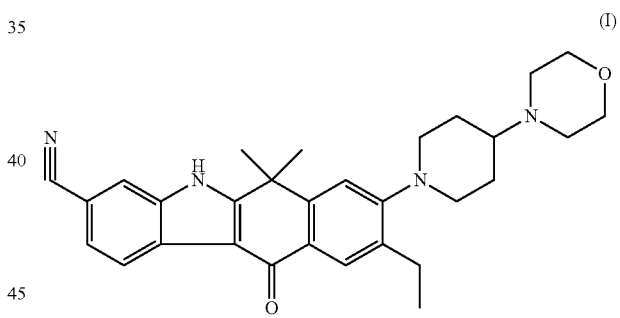

(I)

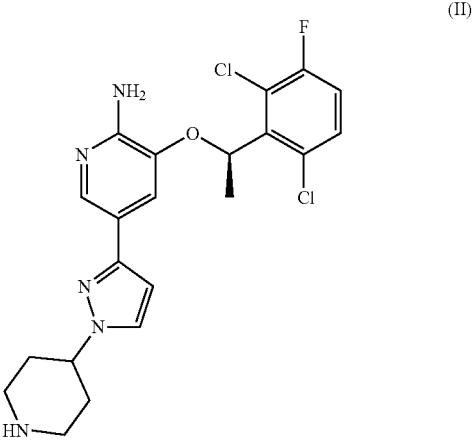

(II)

-continued

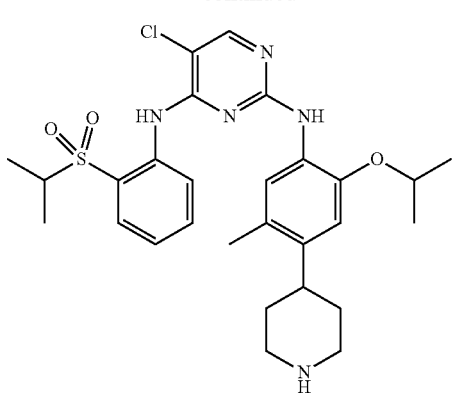

(III)

Either oral or parenteral routes of administration of the ALK inhibitor used in the present invention can suitably be used, but preferably oral administration is suitably used. A dosage form used for oral administration can be selected from any dosage forms such as solutions, powders, granules, tablets, enteric coated tablets and capsules. ALK inhibitors with such dosage forms are formulated in a manner known to a person skilled in the art. For example, they are appropriately combined and mixed in a unit dosage form required for generally-accepted pharmaceutical practices with a pharmacologically acceptable carrier or medium, specifically, sterilized water or physiological saline, vegetable oils, emulsifiers, suspending agents, surfactants, stabilizers, flavoring agents, excipients, vehicles, preservatives and/or binders, and are then formulated by lyophilization, compression, and other processes.

ALK inhibitors can be used parenterally in the form of sterile solutions or suspensions for injection in water or other pharmaceutically acceptable liquid. The amount of an active ingredient in the formulated agents is appropriately selected so that a suitable dose within a designated range can be administered. Sterile compositions for injection can be formulated following ordinary pharmaceutical practices using vehicles such as distilled water for injection. Examples of aqueous solutions for injection include saline, isotonic solutions containing auxiliary medicine of glucose or others such as D-sorbitol, D-mannose, D-mannitol, and sodium chloride, which can be used in combination with an appropriate solubilizing agent, e.g. alcohol such as ethanol, polyalcohol such as propylene glycol and polyethylene glycol, and non-ionic surfactants such as polysorbate 80 (™) and HCO-50. Sesame oil and soybean oil are exemplified as oily liquids, which may be used in combination with benzyl benzoate or benzyl alcohol as a solubilizing agent. Furthermore, they can be suitably formulated with a buffer such as phosphate buffer and sodium acetate buffer, a soothing agent such as procaine hydrochloride, a stabilizer such as benzyl alcohol and phenol or an antioxidant.

The dosage of ALK inhibitor according to the present invention can be selected in a range of, for example, 0.0001 mg to 1000 mg per 1 kg of body weight per dose. Or, the dosage can be selected in a range of, for example, 0.001 mg to 100000 mg/body for each patient. The dosage of ALK inhibitors of the present invention, however, is not limited to these dosages.

A more specific dosage of the alectinib, a salt thereof or a hydrate thereof is two doses of 20 mg, 40 mg, 60 mg, 80 mg, 120 mg, 160 mg, 220 mg, 240 mg, 300 mg, 460 mg, 600 mg, 760 mg or 900 mg calculated as a free form per day.

The administration period of the ALK inhibitor according to the present invention is appropriately determined depending on symptoms or level of side effects. The ALK inhibitor can be administered until a cancer is cured or a desired therapeutic effect is achieved. Specifically, it may be administered from seven consecutive days to three consecutive years. Or, it may be administered in 1 to 36 cycle(s), each of which has 2 days to 3 months, with washout intervals of 1 to 14 day(s). Preferably, the ALK inhibitor is administered in 3 to 24 cycles, each of which has 14 to 30 days.

VEGF Inhibitors

VEGF inhibitors used in the present invention refer to substances that can directly or indirectly neutralize, block, inhibit, reduce, or interfere with VEGF activity. VEGF inhibitors may neutralize, block, inhibit, reduce, or interfere with VEGF activity by binding to one or more VEGF receptors. VEGF inhibitors include anti-VEGF antibodies and their antigen-binding fragments, derivatives that specifically bind to receptor molecules and VEGF to block binding of VEGF to one or more receptors, anti-VEGF receptor antibodies and anti-VEGF receptor antagonists (e.g., low molecular weight inhibitors of VEGFR tyrosine kinase). Specific examples of low molecular weight VEGF inhibitors include compounds selected from the group consisting of sorafenib (compound name: N-(4-Chloro-3-(trifluoromethyl)phenyl)-N'-(4-(2-(N-methylcarbamoyl)-4-pyridyloxy)phenyl)urea, Patent Literature: U.S. Pat. No. 7,235,576), pazopanib (compound name: 5-[[4-[(2,3-dimethyl-2H-indazol-6-yl)methylamino]pyrimidin-2-yl] amino]-2-methylbenzenesulfonamide), sunitinib (compound name: N-[2-(Diethylamino)ethyl]-5-[(Z)-(5-fluoro-2-oxo-1,2-dihydro-3H-indol-3-ylidene)methyl]-2,4-dimethyl-1H-pyrrole-3-carboxamide, Patent Literatures: U.S. Pat. Nos. 3,663,382, 6,573,293, 7,125,905), axitinib (compound name: N-Methyl-2-({3-[(1E)-2-(pyridin-2-yl)ethen-1-yl]-1H-indazol-6-yl}sulfanyl)benzamide), regorafenib (compound name: 4-(4-(((4-chloro-3-(trifluoromethyl)phenyl) carbamoyl}amino)-3-fluorophenoxy)-N-methylpyridine-2-carboxamide), cabozantinib (compound name: 1,1-Cyclopropanedicarboxamide, N'-[4-[(6,7-dimethoxy-4-quinolinyl)oxy]phenyl]-N-(4-fluorophenyl)-), and nintedanib (chemical name: (Z)-methyl 3-((4-(N-methyl-2-(4-methylpiperazin-1-yl)acetamido)phenylamino)(phenyl) methylene)-2-oxoindoline-6-carboxylate, see, WO01/27081), salts thereof, hydrate thereof, and the like.

The term "anti-VEGF antibody" as used herein refers to antibodies that bind to VEGF with a sufficient affinity and specificity. The antibody selected normally has a binding affinity for VEGF. For example, the antibody may bind to hVEGF with a Kd value of 100 nM to 1 pM. Antibody affinity may be determined using a surface plasmon resonance assay (such as a BIAcore assay as described in WO2005/012359), an enzyme-linked immunosorbent assay (ELISA) or a competition assay (such as those of RIA). In another embodiment, the anti-VEGF antibody of the present invention can be used as a therapeutic agent that targets diseases or conditions in which VEGF activity is involved and interferes with the activity. Furthermore, in order to evaluate effectiveness of an antibody as a therapeutic agent, it may be subjected to other biological assay(s) for its activity. Such assays are known in the art and depend on the targeted antigen and the intended use of the antibody. Examples include HUVEC inhibition assays, tumor cell growth inhibition assays (e.g., those described in WO89/06692); antibody-dependent cellular cytotoxicity (ADCC) and complement-mediated cytotoxicity (CDC) assays (U.S.

Pat. No. 5,500,362), and assays for agonist activity or hematopoiesis (see, WO95/27062).

The term "antibody" is used in the broadest sense and encompasses monoclonal antibodies (including full length or intact monoclonal antibodies), polyclonal antibodies, multivalent antibodies, multispecific antibodies (e.g., bispecific antibodies), and their antibody fragments so long as they exhibit the desired biological activity (see below).

The "Kd" or "Kd value" as used herein is measured, in one embodiment by a radiolabeled VEGF binding assay (RIA) performed with a Fab of an antibody and a VEGF molecule as described by the following assay, in which solution binding affinity of the Fab for VEGF is measured by equilibrating the Fab with a minimal concentration of an ($^{125}$I)-labeled antigen in the presence of a titration series of unlabeled VEGF, and capturing VEGF bound to the anti-Fab antibody-coated plates (Chen, et al., (1999) J. Mol Biol 293:865-881). In one example, to determine assay conditions, microtiter plates (Dynex) are coated overnight with 5 µg/ml of an anti-Fab capture antibody (Cappel Labs) in 50 mM sodium carbonate (pH 9.6), and then blocked with 2% (w/v) of bovine serum albumin in PBS for 2 to 5 hours at room temperature (approximately 23° C.). In non-adherent plates (Nunc #269620), 100 pM or 26 pM [$^{125}$I]VEGF(109) is mixed with serial dilutions of a Fab of interest such as Fab-12 (Presta et al., (1997) Cancer Res. 57:4593-4599). Subsequently, the Fab of interest is incubated overnight. The incubation may, however, require 65 hours to ensure equilibrium. The mixtures are then transferred to the capture plates and incubated at room temperature for 1 hour. Thereafter, the solution is removed and the plates are washed eight times with 0.1% Tween20 in PBS. After the plates are dried, scintillant (MicroScint-20; Packard) is added at 150 µl/well, and the plates are subjected to measurement with a Topcount gamma counter (Packard) for 10 minutes. Fab concentrations equal to or lower than 20% of the maximal binding are chosen and used for competitive binding assays. In another embodiment, the Kd or Kd value is measured by a surface plasmon resonance assay with a BIAcore™-2000 or a BIAcore™-3000 (BIAcore, Inc., Piscataway, NJ) at 25° C. using CM5 chips on which hVEGF (8-109) is immobilized at about 10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Human VEGF is diluted with 10 mM sodium acetate (pH 4.8) into 5 µg/ml (ca. 0.2 uM) and injected at a flow rate of 5 ul/min. to achieve approximately 10 response units (RU) of the coupled protein. After the injection of human VEGF, 1 M ethanolamine is injected to block unreacted groups. For kinetics measurements, two-fold serial dilutions of Fab (0.78 nM to 500 nM) are injected into PBS containing 0.05% Tween 20 (PBST) at 25° C. at a flow rate of approximately 25 ul/min. Association rates (Kon) and dissociation rates (Koff) were calculated using a simple one-to-one Langmuir binding model (BIAcore Evaluation Software version 3.2) by simultaneously fitting the association and dissociation sensorgrams. The equilibrium dissociation constant (Kd) was calculated as the ratio Koff/Kon. See, for example, Chen, Y, et al., (1999) J. Mol Biol 293:865-881. If the association rate by the aforementioned surface plasmon resonance assay exceeds 10$^6$M-1S-1, the association rate can be measured using a fluorescent quenching technique by which the increase or decrease in fluorescence emission intensity (excitation=295 nm; emission=340 nm, band-pass=16 nm) of 20 nM anti-VEGF antibody (Fab form) in PBS (pH 7.2), is measured at 25° C. in the presence of increasing concentrations of human VEGF short form (8-109) or mouse VEGF using a spectrometer such as a spectrophotometer equipped with a stop-flow (Aviv Instruments) or a 8000-series SLM-Aminco spectrophotometer (ThermoSpectronic) with a stirred cuvette.

In the present invention, the anti-VEGF antibody or an antigen-binding fragment thereof may be a monoclonal antibody, chimeric antibody, intact human antibody, or humanized antibody. Furthermore, the anti-VEGF antibodies or antigen binding fragments thereof may be Fc portion, F(ab')2, Fab, or an antibody that lacks Fv structure.

In one embodiment of the present invention, examples of the anti-VEGF antibody include, but not limited to, monoclonal antibodies that bind to the same epitope as the anti-VEGF monoclonal antibody A4.6.1 produced by hybridoma ATCC HB 10709 and recombinant humanized anti-VEGF monoclonal antibodies produced according to Presta et al. (1997) Cancer Res. 57:4593-4599. In another embodiment, the anti-VEGF antibody is "bevacizumab (BV)", which is also known as "rhuMAb VEGF" or "AVASTIN (registered trademark)". AVASTIN (registered trademark) is commercially sold in certain countries. It includes antigen-binding complementarity-determining regions from the murine anti-hVEGF monoclonal antibody A.4.6.1 that blocks binding of human VEGF to its receptors and mutated human IgG1 framework regions. Approximately 93% of the amino acid sequence of bevacizumab which includes most of the framework regions is derived from human IgG1, and approximately 7% of the sequence is derived from the murine antibody A4.6.1. As used herein, the term "bevacizumab (BV)" encompass all corresponding anti-VEGF antibodies or anti-VEGF antibody fragments, which fulfill the requirements for obtaining a marketing authorization as an identical or biosimilar product in a country selected from the group of countries consisting of the United States of America, Europe and Japan or a region thereof.

In order to make a screening for antibodies that bind to an epitope on an antigen bound by an antibody of interest, a routine cross-blocking assay such as those described in A Laboratory Manual, Cold Spring Harbor Laboratory, Ed Harlow and David Lane (1988) can be performed.

Bevacizumab and other humanized anti-VEGF antibodies are further described in U.S. Pat. No. 6,884,879 issued on Feb. 26, 2005. Also included are the G6 or B20 series antibodies (e.g., G6-31, B20-4.1) as described in WO2005/012359, WO2005/044853 and U.S. Patent Application No. 60/991,302. In addition, also included are antibodies as described in U.S. Pat. Nos. 7,060,269, 6,582,959, 6,703,020, and 6,054,297, WO98/45332, WO 96/30046, WO94/10202, European Patent No. 0666868B1, U.S. Patent Publication Nos. 2006009360, 20050186208, 20030206899, 20030190317, 20030203409, and 20050112126, and Popkov et al., Journal of Immunological Methods 288:149-164 (2004). In one embodiment, the aforementioned antibodies include those that bind to a functional epitope including residues F17, M18, D19, Y21, Y25, Q89, I91, K101, E103, and C104 or including residues F17, Y21, Q22, Y25, D63, I83 and Q89 on human VEGF.

The aforementioned "G6 series antibody" is an anti-VEGF antibody derived from a sequence of any one of the G6 antibodies and G6-derived antibodies in FIGS. 7, 24-26 and 34-35 of WO2005/012359. Furthermore, antibodies described in WO2005/044853 are also included. In one embodiment, a G6 series antibody binds to a functional epitope including residues F17, Y21, Q22, Y25, D63, I83 and Q89 on human VEGF.

The aforementioned "B20 series antibody" is an anti-VEGF antibody derived from a sequence of any one of the B20 antibodies and B20-derived antibodies in FIGS. 27-29 of WO2005/012359. Furthermore, antibodies described in WO2005/044853 and U.S. Patent Application No. 60/991, 302 are also included. In one embodiment, a B20 series antibody binds to a functional epitope including residues F17, M18, D19, Y21, Y25, Q89, I91, K101, E103, and C104 on human VEGF.

The aforementioned "functional epitope" refers to amino acid residues of an antigen which contribute energetically to antibody binding. Mutation of any one of the energetically contributing residues of the antigen (e.g., mutation of the wild-type VEGF or its homolog by alanine) will disrupt the binding of the antibody such that the relative affinity ratio ($IC_{50}$ mutant VEGF/$IC_{50}$ wild-type VEGF) of the antibody will be greater than 5 (see, Example 2 of WO2005/012359). In one embodiment, the relative affinity ratio is measured by a solution binding phage display ELISA. Briefly, 96-well Maxisorp immunoplates (NUNC) are coated with an Fab form of an antibody at 4° C. overnight, tested in PBS at 2 μg/ml, and blocked with PBS containing 0.5% BSA and 0.05% Tween20 (PBT) at room temperature for 2 hours. In PBT, serial dilutions of phage displaying a hVEGF alanine point mutants (residues 8-109 form) or the wild type hVEGF (8-109) are incubated first on Fab-coated plates at room temperature for 15 minutes, and the plates are washed with PBS containing 0.05% Tween20 (PBST). The bound phages are detected with a horseradish peroxidase-conjugated anti-M13 monoclonal antibody (Amersham Pharmacia) diluted 1:5000 in PBT and developed with a substrate, 3,3',5,5'-tetramethylbenzidine (TMB, Kirkegaard & Perry Labs, Gaithersburg, MD), for approximately 5 minutes. The signal is quenched with 1.0 M $H_3PO_4$ and read spectrophotometrically at 450 nm. The ratio of $IC_{50}$ values ($IC_{50}$, ala/$IC_{50}$, wt) represents the fold of reduction in binding affinity (the relative binding affinity).

"Humanized" forms of non-human (such as murine) antibodies are chimeric antibodies containing minimal sequence derived from non-human immunoglobulin. For the most part, humanized antibodies are human immunoglobulins (recipient antibodies) in which residues in a hypervariable region of a recipient are substituted with those in a hypervariable region of a non-human species (donor antibodies) such as mouse, rat, rabbit or non-human primate having desired specificity, affinity, and capacity. In some examples, framework region (FR) residues of the human immunoglobulin are substituted with the corresponding non-human residues. Furthermore, humanized antibodies may include residues that are found neither in recipient antibodies nor in donor antibodies. These modifications are made to further refine antibody performance. In general, the humanized antibody will include substantially all of at least one and typically two variable domains, in which all or substantially all of the hypervariable loops correspond to those of a non-human immunoglobulin and all or substantially all of the FRs are those of a human immunoglobulin sequence. The humanized antibody also includes, in some cases, at least a portion of an immunoglobulin constant region (Fc), typically at least a portion of that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

Other examples of humanized anti-VEGF antibody include ramucirumab (generic name: ramcirumab, product name: Cyamza™, CAS registry number: 947687-13-0).

In another embodiment of the present invention, the anti-VEGF antibody has a heavy chain variable region produced so as to include the following amino acid sequence: EVQLVESGGG LVQPGGSLRL SCAASGYTFT NYGMNWVRQA PGKGLEWVGW INTYTGEPTY AADFKRRFTF SLDTSKSTAY LQMNSLRAED TAVYYCAKYP HYYGSSHWYF DVWGQGTLVT VSS (SEQ ID NO.: 1); and a light chain variable region including the following amino acid sequence:

```
                                       (SEQ ID NO.: 2)
DIQMTQSPSS LSASVGDRVT ITCSASQDIS NYLNWYQQKP

GKAPKVLIYF TSSLHSGVPS RFSGSGSGTD FTLTISSLQP

EDFATYYCQQ YSTVPWTFGQ GTKVEIKR.
```

The VEGF inhibitors can be formulated according to a conventional method (e.g., Remington's Pharmaceutical Science, the latest edition, Mack Publishing Company, Easton, U.S.A.) and contain a pharmaceutically acceptable carrier or additive. Examples include, but not limited to, surfactants, excipients, colorants, fragrances, preservatives, stabilizers, buffers, suspensions, tonicity agents, binders, disintegrants, lubricants, flow enhancers and flavorings, and other conventional carriers can appropriately be used. Specifically, examples suitably include trehalose, light anhydrous silicic acid, lactose, crystalline cellulose, mannitol, starch, carmellose calcium, carmellose sodium, hydroxypropyl cellulose, hydroxypropylmethyl cellulose, polyvinyl acetal diethylamino acetate, polyvinylpyrrolidone, gelatin, medium-chain fatty acid triglyceride, polyoxyethylene hardened castor oil 60, sucrose, carboxymethylcellulose, corn starch, inorganic salts, and polysorbates.

Medicaments and Methods of Treatment and Prevention

An aspect of the present invention is a medicament for treating or preventing a cancer, which is produced by combining an ALK inhibitor and a VEGF inhibitor.

The "medicament for treating or preventing a cancer, which is produced by combining an ALK inhibitor and a VEGF inhibitor" in the above aspect means a medicament in which an ALK inhibitor and a VEGF inhibitor are combined in order to be administered simultaneously, in separate dosage forms, or sequentially in treating or preventing a cancer. The medicament according to the present invention may be provided in a single dosage form containing both of the ALK inhibitor and the VEGF inhibitor. Furthermore, a formulated agent including the ALK inhibitor and a formulated agent including the VEGF inhibitor may be provided separately and used simultaneously or sequentially.

In the present invention, simultaneous administration refers to administering the ALK inhibitor and the VEGF inhibitor during the same period to use them together. The inhibitors may be administered in a single dosage form, as a mixture freshly prepared at time of administration, or in different dosage forms during the same period. If they are administered simultaneously, they may be administered through different routes or the same route, and in the same dosage form or different dosage forms.

In the present invention, if the ALK inhibitor and the VEGF inhibitor are administered in separate dosage forms, as to the order of administration of the ALK inhibitor and the VEGF inhibitor, the ALK inhibitor may be administered after the administration of the VEGF inhibitor, the ALK inhibitor and the VEGF inhibitor may be administered simultaneously, and the VEGF inhibitor may be administered after the administration of the ALK inhibitor.

Sequential administration of the ALK inhibitor and the VEGF inhibitor according to the present invention means administration of one pharmaceutical agent before administration of the other pharmaceutical agent. A dosing interval of the ALK inhibitor and the VEGF inhibitor is not specifically limited and can be determined in consideration with factors such as their administration routes and their dosage forms. For example, the dosing interval of the ALK inhibitor and the VEGF inhibitor is from 0 to 168 hours, preferably 0 to 72 hours, preferably from 0 to 24 hours, more preferably from 0 to 12 hours. Furthermore, in addition to the factors such as their administration routes and their dosage forms, residual concentrations of each of the ALK inhibitor and the VEGF inhibitor according to the present invention in a subject can also be considered. That is, if the ALK inhibitor is administered before the administration of the VEGF inhibitor, the VEGF inhibitor can be administered at a time when the residual concentration of the ALK inhibitor which will provide a desired effect by the VEGF inhibitor is detected in a subject. This concentration can be determined based on a result obtained by analyzing samples taken from a subject by an analytical method known to a person skilled in the art using a separation device such as various chromatographic devices.

On the contrary, if the VEGF inhibitor is administered before the administration of the ALK inhibitor, the ALK inhibitor can be administered at a time when the residual concentration of the VEGF inhibitor which will provide a desired effect by the ALK inhibitor is detected in a subject. This concentration can be determined based on a result obtained by analyzing samples taken from a subject with an immunological assay such as ELISA known to a person skilled in the art.

In the aforementioned medicaments, when the ALK inhibitor and the VEGF inhibitor are contained in separate formulated agents to be provided, they may be formulated into the same dosage form or different dosage forms. For example, both of them may take different dosage forms, each of which is an oral formulation, a parenteral formulated agent, an injection, an agent for drip infusion, or an agent for intravenous infusion, or both of them may take the same dosage form which is an oral formulation, a parenteral formulated agent, an injection, an agent for drip infusion, and an agent for intravenous infusion. The aforementioned medicament may be combined with one or more additional formulated agents which are different from them.

In another aspect, the present invention provides a medicament used with a VEGF inhibitor to treat or prevent a cancer, including an ALK inhibitor as an active ingredient. The "medicament used with a VEGF inhibitor to treat or prevent a cancer, including an ALK inhibitor as an active ingredient" means a medicament including an ALK inhibitor as an active ingredient, which is used for treating or preventing a cancer in condition that it is used with a VEGF inhibitor. When the medicament including an ALK inhibitor as an active ingredient according to the present invention is used with a VEGF inhibitor, it may be administered simultaneously with the VEGF inhibitor or may be administered before or after the administration of the VEGF inhibitor. If the ALK inhibitor is administered before or after the administration of the VEGF inhibitor, the timing of administration can be optimized by measuring a residual concentration of the VEGF inhibitor in a subject or an expression level of a VEGF isoform as exemplified in Japanese Patent No. 4362225. This concentration can be determined for samples taken from a subject, based on an immunological assay such as ELISA described below known to a person skilled in the art.

In another aspect, the present invention provides a medicament used with an ALK inhibitor to treat or prevent a cancer, including a VEGF inhibitor as an active ingredient. The "medicament used with an ALK inhibitor to treat or prevent a cancer, including a VEGF inhibitor as an active ingredient" in the present invention means a medicament including a VEGF inhibitor as an active ingredient, which is used for treating or preventing a cancer in condition that it is used with an ALK inhibitor. When the medicament including a VEGF inhibitor as an active ingredient is used with an ALK inhibitor, it may be administered simultaneously with the ALK inhibitor or may be administered before or after the administration of the ALK inhibitor. If the VEGF inhibitor is administered before or after the administration of the ALK inhibitor, the timing of administration can be optimized by measuring a residual concentration of the ALK inhibitor in a subject. This concentration can be determined for samples taken from a subject, based on an analytical method known to a person skilled in the art using a separation device such as chromatographic devices.

The above invention means that the ALK inhibitor and the VEGF inhibitor are both administered or used (hereinafter, simply refers to as "administered") and is not interpreted with limited order of administration or dosing interval. It may also be used as a product in which the ALK inhibitor and the VEGF inhibitor of the present invention are combined. Furthermore, when the ALK inhibitor and the VEGF inhibitor are used together in accordance with the present invention, each of them can be administered at a lower dose, if desired, than a dose used when either one of them is administered alone.

Cancers

The medicament according to the present invention is useful for preventing or treating diseases including various cancers such as leukemia (e.g., acute myeloid leukemia, chronic myeloid leukemia, acute lymphoblastic leukemia, and chronic lymphocytic leukemia), malignant lymphoma (e.g., Hodgkin's lymphoma and non-Hodgkin's lymphoma), brain tumors, neuroblastoma, glioma, thyroid cancer, myelodysplastic syndrome, head and neck cancer, esophageal cancer, stomach cancer, colon cancer, colorectal cancer, breast cancer, ovarian cancer, lung cancer, pancreatic cancer, liver cancer, gallbladder cancer, skin cancer, malignant melanoma, kidney cancer, renal pelvis ureter cancer, bladder cancer, uterine cancer, testicular cancer, and prostate cancer. Furthermore, the compounds of the present invention are useful for the prevention or treatment of invasion or metastasis of solid cancers.

In particular, the medicaments of the present invention are useful for the prevention or treatment of cancers positive for an ALK fusion gene. Examples of cancers positive for an ALK fusion gene include, but not limited to, non-Hodgkin's lymphoma, neuroblastoma, inflammatory myofibroblastic tumor, renal cancer, and lung cancer.

In the present invention, the term "positive for an ALK fusion gene" refers to the fact that a fusion gene of ALK and another gene is present. Examples of another fusion gene include, but not limited to, EML4 (echinoderm microtubule-associated protein like protein 4, GenBank™ accession No. NM_019063) and TFG (TRK-fused gene, GeneBank™ accession No. NM_006070).

Method of identifying a cancer positive for an ALK fusion gene is described in, for example, WO2008/127248, JP-A-2008-295444, and "Guidance for ALK Gene Testing" (Biomarker Committee, the Japan Lung Cancer Society). As a kit for detecting the fusion gene, Vysis LSI ALK Break Apart Rearrangement Probe Kit™ (Abbott, Inc.) and Histofine ALK iAEP™ kit (Nichirei Corporation) are sold.

In another aspect of the present invention, provided is a method of enhancing a therapeutic effect of the ALK inhibitor by using a VEGF inhibitor, in treating a patient with a cancer using an ALK inhibitor. Enhancement of a therapeutic effect herein refers to an increase in response rate of the treatment, a reduction in dose of the ALK inhibitor administered for treatment and/or a reduction in duration of treatment using the ALK inhibitor. In another aspect of the present invention, provided is a method of extending a progression-free survival in a subject including administering, in combination, an ALK inhibitor and an effective amount of VEGF inhibitor. In another aspect of the present invention, provided is a method of using a VEGF inhibitor for producing a pharmaceutical composition for treating or preventing a cancer, the composition including an ALK inhibitor and a VEGF inhibitor as active ingredients.

In the present invention, including an ALK inhibitor and/or a VEGF inhibitor as an active ingredient means including the ALK inhibitor and/or the VEGF inhibitor as a major active ingredient and does not limit the contents of the ALK inhibitor and/or the VEGF inhibitor. The term "treatment" means that cancer cells are destroyed or their number is reduced, the proliferation of cancer cells is inhibited, and various symptoms caused by a cancer are improved, by administering the medicament according to the present invention to a subject. Furthermore, the term "prevention" means to prevent increase of decreased cancer cells due to their re-growth, and prevent re-growth of cancer cells of which growth has been inhibited.

In the present invention, administration of the VEGF inhibitor can be achieved either orally or parenterally. Parenteral administration is particularly preferable. Specific examples of such administration suitably include administration by injection, nasal administration, pulmonary administration and transdermal administration. As examples of administration by injection, the therapeutic antibodies of the present invention can be administered systemically or locally by, for example, intravenous injection, intramuscular injection, intraperitoneal injection, and subcutaneous injection. The method of administration may appropriately be selected depending on the age and symptoms of a patient. The dosage can be selected in a dose range of, for example, between 0.0001 mg and 1000 mg per 1 kg of body weight. Or, the dosage can be selected in a range of between 0.001 and 100000 mg/body per patient. The dosage of the VEGF inhibitor of the present invention is, however, not limited to the dosage above.

Depending on the type and severity of the disease, a preferred dose of the anti-VEGF antibody such as bevacizumab can be, but not limited to, in a range of between 1 μg/kg and about 50 mg/kg including 5 mg/kg, 7.5 mg/kg, 10 mg/kg or 15 mg/kg, and most preferably in a range of between about 5 mg/kg and about 15 mg/kg. The frequency of administration varies depending on the type and severity of the disease. With repeated administrations over several days or longer, the treatment is continued until the cancer has been cured or a desired therapeutic effect has been achieved as measured by a method known in the art, depending on the symptom. In one example, the anti-VEGF antibody is administered once a week, once every two weeks, or once every three weeks at a non-limited dose range of between about 5 mg/kg and about 15 mg/kg including 5 mg/kg, 7.5 mg/kg, 10 mg/kg or 15 mg/kg. Other dosage regimens, however, can be useful.

The VEGF inhibitor can be administered until the cancer has been cured or a desired therapeutic effect has been achieved in cycles of once a week, once every two weeks, or once every three weeks. Specifically it can be administered in 1 to 36 cycle(s).

In the present invention, the "progression-free survival (PFS)" refers to the time from treatment (or randomization) to first progression of disease or death. In one aspect of the present invention, PFS can be assessed by Response Evaluation Criteria in Solid Tumors (RECIST). In one aspect of the present invention, PFS can be assessed by CA-125 levels as a determinant of progression.

In the present invention, specific examples of "extending a progression-free survival" include extension of the progression-free survival as compared to that obtained when the ALK inhibitor is administered alone.

In the present invention, a "subject" means a mammal, including, but not limited to, human or a non-human mammal, such as a bovine, equine, canine, ovine or feline to which the medicament of the present invention is to be administered. Preferably, the subject is human. The subject includes patients (including human and non-human mammals).

Products

As another aspect of the present invention, products are provided. In one embodiment, the products are provided to treat or prevent a cancer in a subject which include (a)(1) a formulated agent containing a VEGF inhibitor, (2) a container, and (3) an instruction leaflet or label indicating that the VEGF inhibitor and at least one ALK inhibitor are administered in combination to a subject in order to treat a cancer in the subject or (b)(1) a formulated agent containing an ALK inhibitor, (2) a container, and (3) an instruction leaflet or label indicating that the ALK inhibitor and at least one VEGF inhibitor are administered in combination to a subject in order to treat a cancer in the subject.

The product includes a container containing a formulated agent containing a VEGF inhibitor or an ALK inhibitor.

The product may further include a label or an instruction leaflet on or with the container.

The "instruction leaflet" in the present invention means document typically included in commercial packages of a formulated agent, including information about diseases or symptoms to be treated, usage, dosage, administration, contraindications and/or warning associated with the use of the formulated agent. The "label" means a sheet with an indication of the product name of a formulated agent containing the VEGF inhibitor or the ALK inhibitor, dose, dosage form, and diseases or symptoms to be treated, directly attached to the container.

The label or instruction leaflet indicates diseases or symptoms to be treated or use for selected diseases such as a cancer. In one embodiment, the label or instruction leaflet indicates that the formulated agent can be used for treating a cancer. The label or instruction leaflet may also indicate that the formulated agent can be used for treating other disorders.

Suitable containers include, for example, PTP, bottles, vials, syringes, and blister packs. Container may be made of a variety of materials such as glass or plastic. These containers may further be packed in an outer box made of paper to which the contents described in the aforementioned label have been printed.

The presence or absence of side effects in cases where the ALK inhibitor and the VEGF inhibitor is used together can be examined using well known methods. The "side effects" as used herein means clinical, medical, physical, physiological and/or biochemical effects which are observable and/or measurable in a patient who undergoes treatment of a disease, and which are not part of the intended treatment outcome. Generally, these effects are not desirable with respect to the health condition and/or comfort of the treated subject, health risks for the treated subject and/or tolerability of the treatment for the treated subject. Specific examples of the side effects include neutropenia, leukopenia, bleeding (e.g., gastrointestinal bleeding, pulmonary hemorrhage, and cerebral hemorrhage), high blood pressure, nerve toxicity, fatigue, malaise, loss of appetite, nausea, stomatitis, alopecia, thrombocytopenia, being positive for urinary protein, shock, anaphylaxis, gastrointestinal perforation, fistula, delayed wound healing, thromboembolic disease, hypertensive encephalopathy, hypertensive crisis, reversible posterior leukoencephalopathy syndrome, nephrotic syndrome, bone marrow suppression, infectious disease, congestive heart failure, interstitial pneumonia, thrombotic microangiopathy, interstitial lung disease, liver dysfunction, increase in blood bilirubin, abnormal taste, rash, and increase in blood creatinine. By comparing the frequency and grade of side effects observed when the agents are used together with those observed when each of these agents is administered alone, it can be determined whether side effects are reduced when these agents are used together.

EXAMPLE

All patents and references explicitly cited herein are incorporated by reference in its entirety.

The present invention is specifically described by the description of an example but the present invention is not construed as being limited by this description.

Example 1

Alectinib (oral administration of 3 mg/kg calculated as a free form once a day for 15 days) was administered to severe combined immunodeficiency (SCID) mice, to each of which $1 \times 10^7$ cells of human non-small cell lung cancer cell line NCI-H2228 which is positive for the ALK fusion gene had been transplanted, along with an anti-cancer agent selected from a DNA cross-linking agent cisplatin, a microtubule inhibitor paclitaxel, a DNA synthesis inhibitor gemcitabine, and an anti-human VEGF antibody bevacizumab on day 17 or 20 after the transplantation of the cells. Cisplatin (5 mg/kg) was administered intravenously once a week (Days 17 and 24), paclitaxel (12.5 mg/kg) was administered intravenously once a week (Days 20 and 27), gemcitabine (60 mg/kg) was administered intraperitoneally twice a week (Days 17, 21, 24, and 27), and bevacizumab (5 mg/kg) was administered intraperitoneally once a week (Days 20 and 27). Tumor volumes (mean±standard deviation) and body weight change rates (mean±standard deviation) in these groups are shown in the FIGURE.

In the FIGURE, the horizontal axis represents the number of days elapsed after the transplantation of the cells, and the vertical axis represents the tumor volume and the body weight change rate. Control represents control groups to which a solvent is administered and combo represents combined use groups.

As a result, all of the combined use groups exhibited higher anti-tumor effects as compared with groups to which alectinib had been administered alone. In particular, although increases in tumor volume were observed during the administration of bevacizumab alone which targets angiogenesis, reductions of tumors were observed in the groups to which alectinib and bevacizumab had been administered together, and a statistically significantly greater anti-tumor effect (P=0.008) was shown as compared with the groups to which alectinib had been administered alone. No significant change in tumor volume was observed during the administration of cisplatin, paclitaxel or gemcitabine alone, which are cytotoxic anti-cancer agents.

The invention claimed is:

1. A method of treating a cancer comprising: administering, in combination, an effective amount of ALK inhibitor and an effective amount of VEGF inhibitor to a subject in need thereof, wherein the ALK inhibitor is alectinib or a salt thereof and the VEGF inhibitor is bevacizumab.

2. The method according to claim 1, wherein the ALK inhibitor and the VEGF inhibitor are administered in separate dosage forms.

3. The method according to claim 2, wherein the ALK inhibitor and the VEGF inhibitor are administered simultaneously.

4. The method according to claim 1, wherein the cancer is selected from the group consisting of non-Hodgkin's lymphoma, neuroblastoma, inflammatory myofibroblastic tumor, renal cancer, and lung cancer.

5. The method according to claim 1, wherein the cancer is positive for an ALK fusion gene.

6. A method of suppressing growth of a tumor comprising: administering, in combination, an effective amount of ALK inhibitor and an effective amount of VEGF inhibitor to a subject in need thereof, wherein the ALK inhibitor is alectinib or a salt thereof and the VEGF inhibitor is bevacizumab.

7. The method according to claim 6, wherein the ALK inhibitor and the VEGF inhibitor are administered in separate dosage forms.

8. The method according to claim 7, wherein the ALK inhibitor and the VEGF inhibitor are administered simultaneously.

9. The method according to claim 6, wherein the tumor is selected from the group consisting of non-Hodgkin's lymphoma, neuroblastoma, inflammatory myofibroblastic tumor, renal cancer, and lung cancer.

10. The method according to claim 6, wherein the tumor has an ALK fusion gene.

11. The method according to claim 6, wherein the alectinib or a salt thereof is administered at a dose of 20 mg, 40 mg, 60 mg, 80 mg, 120 mg, 160 mg, 220 mg, 240 mg, 300 mg, 460 mg, 600 mg, 760 mg or 900 mg calculated as a free form twice a day.

12. The method according to claim 6, wherein the bevacizumab is administered at 1 μg/kg to 50 mg/kg.

13. The method according to claim 12, wherein the bevacizumab is administered at 5 mg/kg, 7.5 mg/kg, 10 mg/kg or 15 mg/kg.

14. The method according to claim 12, wherein the bevacizumab is administered once a week, once every two weeks, or once every three weeks.

15. The method according to claim 1, wherein the alectinib or a salt thereof is administered at a dose of 20 mg, 40 mg, 60 mg, 80 mg, 120 mg, 160 mg, 220 mg, 240 mg, 300 mg, 460 mg, 600 mg, 760 mg or 900 mg calculated as a free form twice a day.

16. The method according to claim 1, wherein the bevacizumab is administered at 1 μg/kg to 50 mg/kg.

17. The method according to claim 16, wherein the bevacizumab is administered at 5 mg/kg, 7.5 mg/kg, 10 mg/kg or 15 mg/kg.

18. The method according to claim 16, wherein the bevacizumab is administered once a week, once every two weeks, or once every three weeks.

19. The method according to claim 2, wherein the ALK inhibitor and the VEGF inhibitor are administered sequentially.

20. The method according to claim 7, wherein the ALK inhibitor and the VEGF inhibitor are administered sequentially.

* * * * *

SEQUENCE LISTING

```
<160> NUMBER OF SEQ ID NOS: 2

<210> SEQ ID NO 1
<211> LENGTH: 123
<212> TYPE: PRT
<213> ORGANISM: Homo sapiens

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110
```

```
Trp Gly Gln Gly Thr Leu Val Thr Val Ser Ser
        115                 120

<210> SEQ ID NO 2
<211> LENGTH: 108
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg
            100                 105
```